United States Patent
Mitchell (10) Patent No.: US 10,113,981 B2
(45) Date of Patent: Oct. 30, 2018

(54) REAL-TIME ANALYSIS AND CONTROL OF ELECTRON BEAM MANUFACTURING PROCESS THROUGH X-RAY COMPUTED TOMOGRAPHY

(71) Applicant: Lockheed Martin Corporation, Bethesda, MD (US)

(72) Inventor: Steven Wylie Mitchell, Manassas, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 15/211,566

(22) Filed: Jul. 15, 2016

(65) Prior Publication Data

US 2017/0023499 A1    Jan. 26, 2017

Related U.S. Application Data

(60) Provisional application No. 62/195,108, filed on Jul. 21, 2015.

(51) Int. Cl.
*G01N 23/203* (2006.01)
*G01N 23/04* (2018.01)
*G01N 23/046* (2018.01)
*G01N 23/2252* (2018.01)

(52) U.S. Cl.
CPC ......... *G01N 23/203* (2013.01); *G01N 23/046* (2013.01); *G01N 23/2252* (2013.01); *G01N 2223/419* (2013.01); *G01N 2223/501* (2013.01); *G01N 2223/629* (2013.01); *G01N 2223/646* (2013.01)

(58) Field of Classification Search
CPC .............. G01N 23/203; G01N 23/046; G01N 23/2252; G01N 2223/419; G01N 2223/501; G01N 2223/629; G01N 2223/646
USPC ................. 250/305, 306, 307, 309, 310, 311
See application file for complete search history.

(56) References Cited

U.S. PATENT DOCUMENTS

| | | |
|---|---|---|
| 3,300,618 A | 1/1967 | Sciaky |
| 3,437,785 A | 4/1969 | Sciaky |
| 3,780,256 A | 12/1973 | Mara et al. |
| 4,274,005 A | 6/1981 | Yamamura et al. |
| 5,014,293 A | 5/1991 | Boyd et al. |

(Continued)

OTHER PUBLICATIONS

Search Report and Written Opinion for international application No. PCT/US2016/042506, dated Oct. 21, 2016 (12 pages).

(Continued)

*Primary Examiner* — Nicole Ippolito
(74) *Attorney, Agent, or Firm* — Hamre, Schumann, Mueller & Larson, P.C.

(57) ABSTRACT

Electron beam manufacturing processes, and systems that perform the processes, are described that utilize real-time analysis and control of the electron beam manufacturing processes by detecting secondary x-rays that are generated as a result of the electron beam contacting a workpiece. The detected secondary x-rays are used to generate, in real-time, a three-dimensional cross-sectional image of the portion or region of the workpiece surrounding the location contacted by the electron beam. In addition, real-time analysis of the three-dimensional cross-sectional image can be used to detect defects and real-time re-work or correction of defects can be performed by directing an electron beam back to an area with a defect.

9 Claims, 5 Drawing Sheets

(56) References Cited

U.S. PATENT DOCUMENTS

| | | | |
|---|---|---|---|
| 5,245,191 | A | 9/1993 | Barber et al. |
| 5,305,363 | A | 4/1994 | Burke et al. |
| 6,005,918 | A | 12/1999 | Harris et al. |
| 6,401,001 | B1 | 6/2002 | Jang et al. |
| 8,461,474 | B2 | 6/2013 | Wollenhaupt et al. |
| 8,546,717 | B2 | 10/2013 | Stecker |
| 8,598,523 | B2 | 12/2013 | Stecker et al. |
| 8,809,780 | B2 | 8/2014 | Wollenhaupt et al. |
| 2004/0249495 | A1 | 12/2004 | Orozco et al. |
| 2005/0139768 | A1* | 6/2005 | Bloess ............... G01N 23/2206 250/309 |
| 2008/0061249 | A1* | 3/2008 | Brown ..................... B82B 3/00 250/492.2 |
| 2010/0326962 | A1 | 12/2010 | Calla |
| 2011/0061591 | A1 | 3/2011 | Stecker |
| 2011/0114839 | A1 | 5/2011 | Stecker et al. |
| 2011/0240607 | A1 | 10/2011 | Stecker et al. |
| 2013/0055568 | A1 | 3/2013 | Dusel et al. |
| 2014/0014629 | A1 | 1/2014 | Stecker |
| 2014/0061167 | A1 | 3/2014 | Stecker et al. |
| 2014/0158667 | A1 | 6/2014 | Stecker et al. |
| 2015/0037599 | A1 | 2/2015 | Blackmore |

OTHER PUBLICATIONS

Arata et al., "A Study on Dynamic Behaviours of Electron Beam Welding (Report I): The Observation by a Fluoroscopic Method", Osaka University, Transactions of JWRI, vol. 5, No. 1, 10 pages, Mar. 1976, available at: https://ci.nii.ac.jp/els/contents110006484311.pdf?id=ART0008510393.

Arata et al., Tandem Electron Beam Welding (Report IV): Analysis of Beam Hole Behaviour by Transmission X-Ray Method (Welding Physics, Processes and Instruments), Osaka University, Transactions of JWRI, vol. 11, No. 1, 6 pages, Jun. 1982, available at: https://ci.nii.ac.jp/els/contents110006484311.pdf?id=ART0008510393.

Arata et al., Tandem Electron Beam Welding (Report III): Analysis of Front Wall of Beam Hole by Beam Hole X-ray Observation Method (Welding Physics, Processes & Instruments), Osaka University, Transactions of JWRI, vol. 9, No. 1, 11 pages, Jun. 1980, available at: https://ci.nii.ac.jp/els/contents110006484671.pdf?id=ART0008510930.

Bernd Aschenbach, "Realization of X-Ray Telescopes—from Design to Performance", Exp Astron, vol. 26, pp. 95-109, Apr. 22, 2009, available at: https://link.springer.com/content/pdf/10.1007%2Fs10686-009-9163-8.pdf.

Bauer et al., "High Energy Density Welding Processes", Encyclopedia of Life Support Systems (EOLSS), 9 pages, 2011, available at: https://www.eolss.net/Sample-Chapters/C05/E6-171-06-00.pdf.

Berejka et al., "Industrial Radiation Processing with Electron Beams and X-Rays", International Atomic Energy Agency, Revision 6, 115 pages, May 1, 2011, available at: http://iiaglobal.com/uploads/documents/Industrial_Radiation_eBeam_Xray.pdf.

Bethe et al., "On the Stopping of Fast Particles and on the Creation of Positive Electrons", Proceedings of the Royal Society A: Mathematical, Physical & Engineering Sciences, vol. 146, issue 856, Series A, pp. 83-112, Aug. 1, 1934, available at: http://rspa.royalsocietypublishing.org/content/royprsa/146/856/83.full.pdf.

Castellano et al., "Analytical Model for the Bremsstrahlung Spectrum in the 0.25-20 keV Photon Energy Range", Spectrochimica Acta Part B, vol. 59, pp. 313-319, 2004.

Dixon, R. D., "An Accurate Method for Determining Electron Beam Welding Voltages", Welding Research Supplement, pp. 343-346, Aug. 1973, available at: https://app.aws.org/wj/supplement/WJ_1973_08_s343.pdf.

Dixon, R. D., "Measurements of Noise on the Beam of an Electron Beam Welding Unit", Welding Research Supplement, pp. 51-56, Aug. 1978, available at: http://files.aws.org/wj/supplement/WJ_1978_02_s51.pdf.

Douissard et al., "A Versatile Indirect Detector Design for Hard X-Ray Microimaging", Journal of Instrumentation, pp. 1-28, Sep. 25, 2012, available at: http://iopscience.iop.org/article/10.1088/1748-0221/7/09/P09016/pdf.

Edwards et al., "Electron Beam Additive Manufacturing of Titanium Components: Properties and Performance", Journal of Manufacturing Science and Engineering, vol. 135, issue 6, 7 pages, Dec. 2013.

Elmer, John, "Standardizing the Art of Electron-Beam Welding", Science & Technology Review, Lawrence Livermore National Laboratory, pp. 11-13, Mar./Apr. 2008.

Germer, Rudolf, "X-Ray Flash Techniques", Journal of Physics E: Scientific Instruments, vol. 12, No. 5, 16 pages, 1979.

Rokhlin et al., "Computerized Radiographic Sensing and Control of an Arc Welding Process", Welding Journal, vol. 69, No. 3, pp. 83-97, Mar. 1990.

Hampel et al., "Experimental Ultra Fast X-Ray Computed Tomography with a Linearly Scanned Electron Beam Source", Flow Measurement and Instrumentation, vol. 16, pp. 65-72, 2005.

Harms et al., "X-Ray Tomography Inspection of SRF Cavities", Proceedings of SRF2011, 5 pages, 2011 available at: https://accelconf.web.cern.ch/accelconf/SRF2011/papers/weioa05.pdf.

Huang, Jianglin, "The Characterisation and Modelling of Porosity Formation in Electron Beam Welded Titanium Alloys", Ph. D. Dissertation, School Metallurgy and Materials, the University of Birmingham, 201 pages, Sep. 2011, available at: http://etheses.bham.ac.uk/3276/1/Huang_12_PhD.pdf.

Johnson, L.D., "Some Observations on the Electron Beam Welding of Copper", Welding Research Supplement, pp. 55-60, Feb. 1970, available at: http://files.aws.org/wj/supplement/WJ_1970_02_s55.pdf.

Kanzler et al., "Probability of Defect Detection of Posiva's Electron Beam Weld", BAM, Federal Institute for Materials Research and Testing, Working Report, 92 pages, Dec. 2013.

Koike et al., "Evaluation of Titanium Alloys Fabricated Using Rapid Prototyping Technologies—Electron Beam Melting and Laser Beam Melting", Materials, vol. 4, No. 10, pp. 1776-1792, Oct. 10, 2011, available at: http://www.mdpi.com/1996-1944/4/10/1776/htm.

Krmar et al., "A Simple Method for Bremsstrahlung Spectra Reconstruction From Transmission Measurements", Medical Physics, vol. 29, No. 6, pp. 932-938, Jun. 2002.

Lacki et al., "Numerical Simulation of the Electron Beam Welding Process", Computers and Structures, vol. 89, issues 11-12, pp. 977-985, Jun. 2011.

Lucas John, Laser Beam vs. Electron Beam Welding Which Process Works Best for What?, NASA Tech Briefs, 87 pages, May 2011.

Mara et al., "Penetration Mechanisms of Electron Beam Welding and the Spiking Phenomenon", Welding Research Supplement, pp. 246-251, Jun. 1974, available at: https://app.aws.org/wj/supplement/WJ_1974_06_s246.pdf.

Matthews et al., "Accurate Formulae for the Calculation of High Energy Electron Bremsstrahlung Spectra", Nuclear Instruments and Methods, vol. 111, issue 1, pp. 157-168, Aug. 1973.

McCall, Gene H., "Calculation of X-Ray Bremsstrahlung and Characteristic Line Emission Produced by a Maxwellian Electron Distribution", Journal of Physics D: Applied Physics, vol. 15, No. 5, pp. 823-831,1982.

Ming-der et al., "Optimisation of Electron-Beam Surface Hardening of Cast Iron for High Wear Resistance Using the Taguchi Method", the International Journal of Advanced Manufacturing Technology, vol. 24, pp. 190-198.

Miyata, Emi, "Broadband X-ray Detector Using CCDs and Scintillators", International Symposium on Detector Development for Particle, Astroparticle and Synchrotron Radiation Experiments, Stanford, California, USA, 8 pages, Apr. 3-6, 2006.

Natour, "Analysis of Materials and Structures in Scientific Applications Using Micro Focus Computed Tomography", Key Engineering Materials, vol. 163, pp. 239-243, May 2014.

Pavlovich et al., "The Total Reliability of NDT Methods for Inspection of the EB Weld of the Copper Canister Used for a Long-Term Storage of Spent Nuclear Fuel", Structural Integrity and NDE Reliability II, 5 pages, 2010.

(56) References Cited

OTHER PUBLICATIONS

Fu et al., "Microstructures and Fatigue Properties of Electron Beam Welds with Beam Oscillation for Heavy Section TC4-DT Alloy", Chinese Journal of Aeronautics, vol. 27, No. 4, pp. 1015-1021, 2014, available at: https://www.sciencedirect.com/science/article/pii/S1000936114000521.

Pitkänen et al., "Defect Detectability in EB-Welded Copper Disposal Canister with 9 MeV Accelerator", 6th International Conference on NDE in Relation to Structural Integrity for Nuclear and Pressurized Components, Budapest, Hungary, Developments in Radiographic Inspection Methods, 16 pages, Oct. 2007, available at: https://www.ndt.net/article/jrc-nde2007/papers/13_18-33.pdf.

Reed et al., "Process Modelling of Electron Beam Welding of Aeroengine Components", Superalloys, pp. 665-674, 2000, available at: http://www.tms.org/superalloys/10.7449/2000/superalloys_2000_665_674.pdf.

Seltzer et al., "Bremsstrahlung Spectra From Electron Interactions with Screened Atomic Nuclei and Orbital Electrons", Nuclear Instruments and Methods, vol. 12, No. 1, pp. 95-134, 1985.

Seufzer et al., "Control of Space-Based Electron Beam Free Form Fabrication", 18th Annual Solid Freeform Fabrication Symposium, Aug. 6-8, 2007; Austin, Texas, USA, 9 pages, Aug. 6, 2007, available at: https://ntrs.nasa.gov/archive/nasa/casi.ntrs.nasa.gov/20070030308.pdf.

Shao et al., "Automatic Weld Detect Detection in Real-Time X-Ray Images Based on Support Vector Machine", 4th International Congress on Image and Signal Processing, vol. 4, pp. 1842-1846, Oct. 2011, available at: https://www.researchgate.net/publication/235411888_Automatic_weld_defect_detection_in_real-time_X-ray_images_based_on_support_vector_machine.

Small et al., "Modeling of the Bremsstrahlung Radiation Produced in Pure-Element Targets by 10-40 keV Electrons", Journal of Applied Physics, vol. 61, No. 2, pp. 459-469, Jan. 15, 1987.

Smith, D. M., "Hard X-Ray and Gamma-Ray Detectors", Physics Department and Santa Cruz Institute for Particle Physics University of California, Santa Cruz, USA, 18 pages, 2010, available at: https://arxiv.org/pdf/1010.4069v1.pdf.

Stampanoni et al., "Computer Algebra for X-Ray Spectral Reconstruction Between 6 and 25 MV", Medical Physics, vol. 28, No. 3, pp. 325-327, Mar. 9, 2001.

Elmer et al., "Tomographic Imaging of Noncircular and Irregular Electron Beam Current Density Distributions", Welding Research Supplement, pp. 493-505, Nov. 1993, available at: http://files.aws.org/wj/supplement/WJ_1993_11_s493.pdf.

Trincavelli et al., "The Prediction of Thick Target Electron Bremsstrahlung Spectra in the 0.25-50 keV Energy Range", Spectrochimica Acta Part B, vol. 63, No. 1, pp. 1-8, 2007.

Trincavelli et al., "Standardless Quantification Methods in Electron Probe Microanalysis", Spectrochimica Acta Part B, vol. 101, pp. 76-85 , 2014.

Trushnikov et al., "Plasma Charge Current for Controlling and Monitoring Electron Beam Welding with Beam Oscillation", Sensors, vol. 12, No. 12, pp. 17433-17445, Dec. 2012, available at: https://www.ncbi.nlm.nih.gov/pmc/articles/PMC3571846/.

Tucker et al., "Semiempirical Model for Generating Tungsten Target X-Ray Spectra", Medical Physics, vol. 18, No. 211, 9 pages, Mar. 1991.

Weber et al., "Penetration Mechanism of Partial Penetration Electron Beam Welding", Welding Research Supplement, pp. 90-96, Feb. 1972, available at: http://files.aws.org/wj/supplement/WJ_1972_02_s90.pdf.

Xu et al., "Real-Time 3D Computed Tomographic Reconstruction Using Commodity Graphics Hardware", Physics in Medicine and Biology, vol. 52, No. 12, pp. 3405-3419, May 17, 2007.

Koglin et al., "NuSTAR hard X-Ray Optics Design and Performance", SPIE Conference on Optics for EUV, X-Ray, and Gamma-Ray Astronomy IV, San Diego, CA, USA, 9 pages, 2009.

Goebbels et al., "Flaw Evaluation in Copper Weldings with Computed Tomography", European Conference on Non-Destructive Testing (ECNDT), 1 page, 2006, Abstract only is enclosed, available at: https://www.ndt.net/article/ecndt2006/doc/We.3.7.5%20Abstract.pdf.

Chen et al., "Weld Defects Detection for X-Ray Linear Array Real-Time Imaging", vol. 28, No. 6, pp. 81-84, Jun. 2007, Abstract only is enclosed.

Kramers H.A., "On the Theory of X-Ray Absorption and of the Continuous XRay Spectrum", The London, Edinburgh, and Dublin Philosophical Magazine and Journal of Science, vol. 43, issue 6, pp. 836-871, 1923.

\* cited by examiner

FIG. 5

REAL-TIME ANALYSIS AND CONTROL OF ELECTRON BEAM MANUFACTURING PROCESS THROUGH X-RAY COMPUTED TOMOGRAPHY

FIELD

This technical disclosure relates to an electron beam manufacturing process, such as electron beam welding or electron beam additive manufacturing, and to the use of secondary x-rays generated from the electron beam contacting a workpiece to analyze results of the manufacturing process and to correct defects in the manufacturing process in real-time.

BACKGROUND

The use of electron beams in manufacturing processes such as electron beam welding and electron beam additive manufacturing are known.

In the case of electron beam welding, the current process is to create a weld joint using the electron beam, allow the weldment to cool, inspect the weld using one or more non-destructive techniques such as x-rays, analyze the inspection data, and re-work the weld if unacceptable defects are found. These steps take time and skilled labor to perform.

U.S. Pat. No. 8,809,780 describes an electron beam additive manufacturing process that performs real-time automated monitoring and control of the process using detection of electron scatter to monitor the pool of molten material being deposited.

SUMMARY

Electron beam manufacturing processes, and systems that perform the processes, are described that utilize real-time analysis and control of the electron beam manufacturing processes by detecting secondary x-rays that are generated as a result of the electron beam contacting a workpiece. The detected secondary x-rays are used to generate, in real-time, a three-dimensional cross-sectional image of the portion or region of the workpiece surrounding the location contacted by the electron beam. In addition, real-time analysis of the three-dimensional cross-sectional image can be used to detect defects, and real-time re-work or correction of defects can be performed by re-directing an electron beam back to an area with a defect to re-work the workpiece.

The electron beam manufacturing processes encompassed herein can include, but are not limited to, any process where an electron beam is directed towards and contacts a workpiece with enough energy to generate secondary x-rays as a result of contacting the workpiece. Examples of electron beam manufacturing processes can include, but are not limited to, electron beam welding and electron beam additive manufacturing. In electron beam welding, an electron beam is directed toward an intended weld joint between two structures to be welded together, with the electron beam creating the weld joint either with or without the introduction of additive material. In electron beam additive manufacturing, an electron beam is used to build up a workpiece layer-by-layer by liquifying an additive material and depositing the liquified material layer-by-layer to form a desired article of manufacture as described in U.S. Pat. No. 8,809,780, the entire contents of which are incorporated herein by reference. In an alternative implementation of electron beam additive manufacturing, the electron beam is used to build up a workpiece layer-by-layer by partially melting an additive material and depositing the partially melted material layer-by-layer to form a desired article of manufacture as described in U.S. Pat. No. 6,401,001, the entire contents of which are incorporated herein by reference.

The electron beam manufacturing processes encompassed herein combine the formerly sequential steps of electron beam processing, inspection, and re-work into a single, integrated, real-time process step. The inspection uses the secondary x-rays produced by the electron beam contacting the workpiece to generate a three-dimensional cross-sectional image of the portion of the workpiece surrounding the location contacted by the electron beam. The three-dimensional cross-sectional image can be generated by using, for example, conventional transmission computed tomography (TCT) techniques. The inspection can also use real-time automated and/or human analysis of the three-dimensional cross-sectional image to detect defects. If a defect is detected, an electron beam can be controlled in real-time to re-work the area containing the defect.

As used herein, the term real-time, unless otherwise defined in this description or claims, is intended to be construed broadly. For example, in one embodiment real-time can mean that the generation of the three-dimensional cross-sectional image, the inspection, and the re-work or correction of defects occurs during the electron beam manufacturing process relatively shortly after the workpiece has been structurally modified by the electron beam, and in some embodiments without requiring the workpiece to cool. For example, in the case of electron beam welding that produces a weld joint, in one embodiment the image generation, the inspection and the re-work (if any) of a portion of the weld joint occurs very shortly after the portion of the weld joint is created, perhaps even before the remainder of the weld joint is created, without removing the workpiece from a chamber of the electron beam welding apparatus. In another example, in the case of electron beam welding that produces a weld joint, real-time can mean that the re-working could be performed after the weld is finished. This could mean that the weld might solidify in the mean-time, which would increase the energy required to re-heat the weld in preparation for re-working, but the benefits of not having to remove the workpiece for inspection before rework would still be obtained. The term real-time can encompass any re-working that occurs during or after the electron beam manufacturing process without removing the workpiece for inspection or conducting a separate inspection (separate from the inspection that takes place during the manufacturing process) of the workpiece prior to re-work.

In one embodiment described herein, a process includes detecting secondary x-rays resulting from an electron beam contacting a portion of a workpiece with sufficient energy to generate the secondary x-rays. As the electron beam continues to contact the workpiece, the detected secondary x-rays are used to generate a three-dimensional cross-sectional image of the portion of the workpiece surrounding the location contacted by the electron beam. In addition, as the electron beam continues to contact the workpiece, the generated three-dimensional cross-sectional image is analyzed to detect a defect in the portion of the workpiece. If a defect is detected, an electron beam, which can be the same electron beam or a different electron beam, is used to correct the detected defect in the portion of the workpiece.

In another embodiment, a real-time process of detecting and correcting a defect during an electron beam manufacturing process on a workpiece is described. As the electron beam is directed onto a portion of the workpiece with sufficient energy to generate secondary x-rays, the secondary x-rays generated from the electron beam contacting the portion of the workpiece are detected. In real-time, transmission computed tomography is used to generate, from the detected secondary x-rays, a three-dimensional cross-sectional image of the portion of the workpiece surrounding the location contacted by the electron beam. In addition, in real-time, the generated three-dimensional cross-sectional image is analyzed to detect a defect in the portion of the workpiece contacted by the electron beam. If a defect is detected, an electron beam is used in real-time to correct the defect.

A system of real-time detecting and correcting a defect during an electron beam manufacturing process on a workpiece is also described. In one embodiment, the system can include an electron beam generator that generates an electron beam, a vacuum chamber containing the workpiece, an array of x-ray sensors that sense secondary x-rays produced by an electron beam generated by the electron beam generator contacting the workpiece, an image generator connected to the array of x-ray sensors that generates a three-dimensional cross-sectional image from detected x-rays using transmission computed tomography, and a controller connected to the electron beam generator (or to a separate electron beam generator) to re-direct an electron beam on to an area found to have a defect to re-work the area and correct the defect. Optionally, a graphical display device can be connected to the image generator for displaying the three-dimensional cross-sectional image.

DRAWINGS

FIG. 5 illustrates a display device that is displaying an example representation of what a three-dimensional cross-sectional image that is generated as described herein may look like.

DETAILED DESCRIPTION

An electron beam manufacturing process is described below that uses real-time analysis and control of the electron beam manufacturing process by detecting secondary x-rays that are generated as a result of the electron beam contacting a workpiece. The detected secondary x-rays are used to generate, in real-time, a three-dimensional cross-sectional image of the portion or region of the workpiece surrounding the location contacted by the electron beam. In addition, real-time analysis of the three-dimensional cross-sectional image can be used to detect defects in an area of the workpiece that has been modified by the electron beam, and real-time re-work or correction of defects can be performed by directing an electron beam back to an area with a defect.

Electron beam manufacturing processes intended to be encompassed within this disclosure can include, but are not limited to, any process where an electron beam is directed towards and contacts a workpiece with enough energy to generate secondary x-rays as a result of the electron beam contacting the workpiece. One example of an electron beam manufacturing process includes, but is not limited to, electron beam welding discussed below with respect to FIG. 3. As discussed further below, in electron beam welding, an electron beam is directed toward an intended weld joint between two structures to be welded together, with the electron beam creating the weld joint either with or without the introduction of additive material. Another example of an electron beam manufacturing process includes, but is not limited to, electron beam additive manufacturing discussed below with respect to FIG. 4. In electron beam additive manufacturing, an electron beam is used to build up a workpiece layer-by-layer by liquifying or partially melting an additive material which is deposited layer-by-layer to form a desired article of manufacture.

Figure 1:
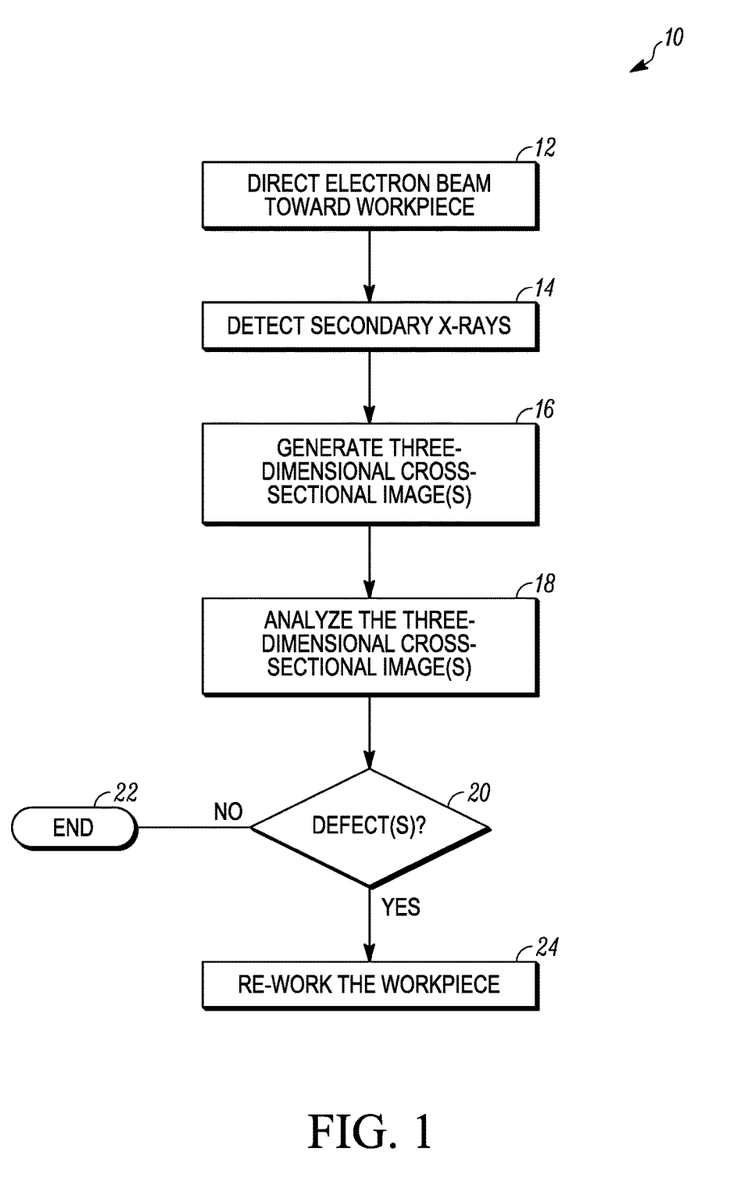
FIG. 1 is a flow chart of an electron beam manufacturing process described herein.

With reference initially to FIG. 1, an electron beam manufacturing process 10 is illustrated. In the process 10, after mounting the workpiece to be processed in a suitable electron beam processing apparatus, an electron beam is directed toward a workpiece at 12. The electron beam is directed at and contacts the workpiece with sufficient energy to generate secondary x-rays as a result of the electron beam contacting the workpiece. Secondary x-rays are x-rays that are emitted from the workpiece as a result of a non-x-ray primary beam, like the electron beam, being incident on the workpiece. The secondary x-rays are generated at the point or region of impact on the workpiece, but they travel through all of the workpiece surrounding the impact point. Therefore, the resulting TCT three-dimensional cross-sectional image that is generated as discussed further below includes all of the workpiece traversed by the x-rays and not just the point of impact.

The workpiece contacted by the electron beam depends on the manufacturing process. In the example of electron beam welding, the workpiece can be a joint between two structures that are to be welded to one another along a weld seam.

In the example of electron beam additive manufacturing, the electron beam may impact a wire that provides the additive material and liquifies it, with the molten material dripping into a weld pool. In this case, the melting wire is typically in contact with the weld pool. The weld pool forms initially on a platform, and later, as layers are built up, on the object being manufactured. As the weld pool solidifies, the layer of the object being manufactured is deposited. Alternatively, the electron beam may impact on a layer of powder spread over the platform (or object being manufactured). In this case, the electron beam partially or completely melts the powder. As the powder solidifies, that material is added to the object being manufactured. In yet another implementation, the electron beam impacts on powder being projected at the platform (or object being manufactured). The electron beam partially or completely melts the powder, which then impacts the platform or the object being manufactured. On impact, the material begins solidifying and is added to the object being manufactured.

As described above, the secondary x-rays are generated at the point of impact of the electron beam on the wire or powder (in the case of additive manufacturing) or on the weldment (in the case of electron beam welding). Everything the secondary x-rays pass through is imaged by the TCT process discussed further below.

The workpiece can be made of metal, ceramic, combinations thereof, and any other material in existence or created in the future that can withstand the energy levels of the electron beam without the electron beam destroying the workpiece.

The electron beam also modifies the workpiece. For example, in electron beam welding, the electron beam temporarily vaporizes the material of the workpiece where the electron beam contacts the workpiece, and liquifies additional material around the point of contact. As the electron beam is moved away, some of the vaporized material liquifies and then the liquified material solidifies to create the weld. In some embodiments, an additive weld material can be utilized in electron beam welding, where the electron beam is used to liquify the additive weld material which is deposited into the joint between the structures being welded and solidifies to create the weld, whereby the deposition of the additive weld material modifies the workpiece. In electron beam additive manufacturing, the deposition of each layer modifies the workpiece.

Returning to FIG. 1, the secondary x-rays that are emitted as a result of the electron beam contacting the workpiece are detected at 14. The detection is performed in real-time (for example within fraction of seconds after the electron beam contacts the workpiece) by an array of x-ray sensors that are suitably arranged relative to the workpiece to permit detection of the secondary x-rays and from the detected secondary x-rays permit creation of a three-dimensional cross-sectional image. Examples of suitable x-ray sensor arrays that can be used include, but are not limited to the Teledyne Rad-icon 1520 (3030) available from Teledyne DALSA of Waterloo, Ontario, Canada; the Perkin Elmer XRD-1642 available from PerkinElmer Inc. of Waltham, Mass.; the Varian Paxscan 2530 HE available from Varian Medical Systems, Inc. of Palo Alto, Calif.; and the Rayonix MX425-HS available from Rayonix, LLC of Evanston, Ill. One or more of the sensor arrays can be provided to perform the detection function and located at sufficient relative positioning to the workpiece to permit creation of the three-dimensional cross-sectional image.

The detected secondary x-ray data is then used at 16 to generate a three-dimensional cross-sectional image of the portion of the workpiece surrounding the location contacted by the electron beam. The three-dimensional cross-sectional image can optionally be displayed on a graphical display device such as on a monitor of a computer workstation, a monitor of a personal computer, on a monitor of a tablet device, or other suitable display device capable of displaying a three-dimensional cross-sectional image. In one embodiment, the three-dimensional cross-sectional image can be generated by TCT. In x-ray TCT, x-ray transmission is measured along multiple paths. Algorithms are used to reconstruct the density profile of the object in a slice, for example using tomographic reconstruction by computing the inverse Radon transformation using deterministic algorithms including filtered back projection, or iterative algorithms like maximum likelihood expectation maximization (MLEM). Density profiles of multiple slices are then used to reconstruct the volumetric density of the object. Creating three-dimensional cross-sectional images using x-ray TCT is a well-known technique. For example, the use of TCT in medical imaging using x-rays is well-known. In addition, the creation of three-dimensional cross-sectional images of welds using x-ray TCT is described by Natour et al. in "Analysis of materials and structures in scientific applications using micro focus computed tomography," 11th International Symposium on Measurement Technology and Intelligent Instruments, ISMTII 2013, Jul. 1, 2013-Jul. 3, 2013. Source: Key Engineering Materials, v 613, p 239-243, 2014; which is incorporated herein by reference in its entirety. However, any other technique for creating the three-dimensional cross-sectional image from the detected secondary x-rays can be used.

The three-dimensional cross-sectional image is generated in real-time and continuously as the electron beam tracks across the workpiece. For example, in one embodiment the three-dimensional cross-sectional image can be generated within about 3-5 seconds or less after the secondary x-rays are detected. In another embodiment, the three-dimensional cross-sectional image can be generated in about 1 second or less after the secondary x-rays are detected. As the electron beam contacts the workpiece and generates the secondary x-rays, the secondary x-rays are detected and the three-dimensional cross-sectional image of the portion of the workpiece surrounding the location contacted by the electron beam is generated and optionally displayed. As the electron tracks across the workpiece, the resulting secondary x-rays are continuously detected and three-dimensional cross-sectional images of all portions of the workpiece surrounding the locations contacted by the electron beam are generated. Therefore, in the case of electron beam welding, a three-dimensional cross-sectional image of the weld zone, along with an image of the surrounding material, can be generated. In the case of electron beam additive manufacturing, a three-dimensional cross-sectional image of the object being manufactured as each layer is being added can be generated.

The three-dimensional cross-sectional images are generated using one or more processors, for example one or more graphical processing units, that are programmed to process the data from the detected secondary x-rays and generate the three-dimensional cross-sectional images, for example using TCT.

Returning to FIG. 1, the generated three-dimensional cross-sectional image is then analyzed at 18 to detect in real-time whether any defects exist in the modified portion of the workpiece. For example, in one embodiment, the analysis results in defect detection within about 5-7 seconds or less after the secondary x-rays are detected. In another embodiment, the analysis results in defect detection within about 3 seconds or less after the secondary x-rays are detected. In the case of additive manufacturing, it is believe at this time to be desirable to fix any defects before another layer is added on top, and so the analysis, detection of defects and rework should occur in that time frame.

The analysis can be automated, performed by one or more human(s), or a combination of automated and human performed. In the case of automated analysis, suitable processing algorithms executed by one or more data processors can perform automated detection of any defects. Automated analysis and detection of defects in x-ray generated TCT images of welds is known from Natour et al. "Analysis of materials and structures in scientific applications using micro focus computed tomography," 11th International Symposium on Measurement Technology and Intelligent Instruments, ISMTII 2013, Jul. 1, 2013-Jul. 3, 2013. Source: Key Engineering Materials, v 613, p 239-243, 2014. In addition, automatic analysis and detection of defects in x-ray images of welds is disclosed in, for example, Shao et al. "Automatic weld defect detection in real-time X-ray images based on support vector machine", Proceedings—4th International Congress on Image and Signal Processing, CISP 2011, v 4, p 1842-1846, Oct. 15, 2011-Oct. 17, 2011; and Sun et al., "A fast and adaptive method for automatic weld defect detection in various real-time X-ray imaging systems," China Welding (English Edition), v 21, n 1, p 8-12, March 2012.

In one embodiment of automated analysis, a three-dimensional cross-sectional model of what the workpiece should look like can be pre-generated. During processing by the electron beam, the three-dimensional cross-sectional image generated from the secondary x-rays can then be compared to the pre-generated three-dimensional cross-sectional model to determine if defects may exist. The comparison can include, for example, determining if a detected value of the generated three-dimensional cross-sectional model exceeds a threshold value relative to the pre-generated three-dimensional cross-sectional model. If the threshold value is exceeded, a determination can be made that a defect may exist.

In the case of human analysis, a human operator can visually monitor the three-dimensional cross-sectional image displayed on the graphical display device in real-time as the electron beam tracks across the workpiece. Based on the experience of the operator, the operator can determine in real-time from the displayed three-dimensional cross-sectional image whether a defect in the modification of the workpiece has occurred.

Returning to FIG. 1, the process 10 proceeds to decision point 20 where it is determined whether or not a defect exists. If the decision at decision point 20 is no (i.e. no defects are detected), the process 10 ends 22. On the other hand, if the decision at decision point 20 is yes (i.e. one or more defects are detected), the portion(s) of the workpiece containing a defect(s) can be re-worked in real-time at 24.

When the analysis at 18 determines that a defect exists, one or more electron beam(s) can be directed in real-time to that portion(s) of the workpiece containing the defect(s) in order re-work or re-modify that portion(s) of the workpiece. The electron beam(s) used to perform re-work can be the same electron beam that initially modified the workpiece, with the electron beam being re-directed to conduct the re-work. In another embodiment, one or more electron beams that are separate from the initial electron beam and possibly produced by separate electron beam generators can be used to conduct the re-work.

In one embodiment, the re-working by an electron beam can be done immediately upon detection of a defect. For example, current processing by the electron beam can be temporarily stopped and the electron beam re-directed back to the defect to re-work the workpiece as quickly as possible after a defect is detected. Alternatively, the electron beam can continue its processing, but a separate, second electron beam can be generated and used to conduct the re-work while the first electron beam continues processing.

In another embodiment, the re-work can be done at some time after detection of a defect, but prior to terminating processing on the workpiece by the electron beam. For example, any re-working of defects can occur after the electron beam has finished processing other portions of the workpiece. In an embodiment where the electron beam is re-directed to perform re-work, the re-direction of the electron beam can be achieved automatically by the control system that controls the electron beam. In addition, the re-direction of the electron beam can be achieved manually by a human operator.

Re-working of defects can be controlled via suitable control logic that is provided to determine the optimal re-work strategy. In addition to determining when re-work should occur, the control logic can determine the order of defect re-working (for example, fixing the first detected defect first, or fix the last detected defect first), as well as the amount of re-work that may be required including controlling the energy of the electron beam to achieve the re-work.

Figure 2:
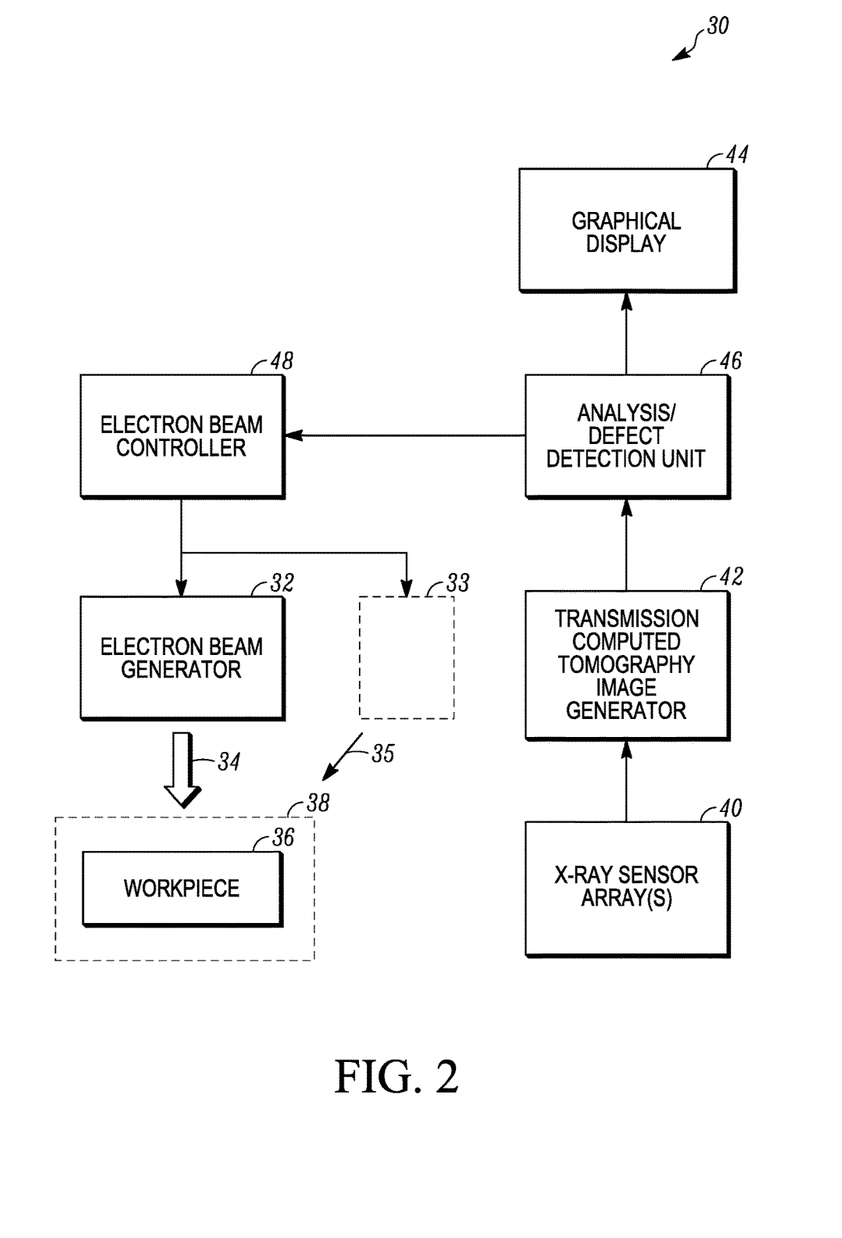
FIG. 2 is a schematic illustration of a system that can implement the electron beam manufacturing process of FIG. 1.

FIG. 2 is a schematic illustration of a system 30 that can implement the electron beam manufacturing process 10. The system 30 can include an electron beam generator apparatus 32 of known construction. The apparatus 32 generates an electron beam 34 that is directed onto a workpiece 36 that is disposed within a vacuum chamber apparatus 38. One or more x-ray sensor arrays 40 are arranged on or in the vacuum chamber apparatus 38 relative to the workpiece 36 to detect the secondary x-rays that result as the electron beam 34 contacts the workpiece 36. Data from the x-ray sensor array(s) 40 is provided to a TCT image generator 42 that can include the software algorithms and the processor(s), for example one or more graphical processing units, that process the data and generate the three-dimensional cross-sectional image. The three-dimensional cross-sectional image generated by the image generator 42 can be displayed on an optional graphical display device 44. In the case when automated analysis is utilized, an analysis/defect detection unit 46 can be provided that includes the processing algorithm(s) executed by one or more data processors to perform the automated analysis of the image and detection of any defects.

Optionally, one or more additional electron beam generator apparatus 33 can be provided that generate one or more additional electron beams 35. When an additional electron beam generator apparatus 33 is provided, the electron beam 34 can be used to process the workpiece, while the electron beam 35 produced by the apparatus 33 can be used to conduct re-working of defects.

The system 30 can also include an electron beam controller 48 that controls the electron beam generator 32 and/or the electron beam generator apparatus 33 to perform reworking of any defects. The electron beam controller 48 can also optionally include the control logic that determines the optimal re-work strategy.

Each of the elements in the system 30 illustrated in FIG. 2 can have any construction that is suitable for achieving the described functions of the elements. In addition, one or more of the elements in the system 30 can be combined with other elements in the system 30, and some of the elements in the system can be separated into separate elements or sub-units. For example, the image generator 42 and the analysis/detection unit 46 can be combined together as part of an integrated unit where the image generator 42 and the analysis/detection unit 46 are sub-units of the integrated unit.

Example Application—Electron Beam Welding

The conventional electron beam welding process is to mount a workpiece in a vacuum chamber, direct an electron beam onto a joint to create a weld, allow the weldment to cool so that it can be handled, inspect the weld using various non-destructive techniques such as X-rays, analyze the inspection data, and re-work the weld if unacceptable defects are detected. The process 10 described above combines all of these steps into one by detecting the secondary x-rays during welding for real-time TCT imaging, combined with real-time inspection and re-working to detect and correct weld defects in real-time.

Defects in welds can lead to catastrophic structural failures. Examples of weld defects that can arise in electron beam welding include, but are not limited to, internal root defects, void or cavities caused by spiking, gas porosity, excess penetration by the electron beam, cavities, and defects caused by electron gun discharge. To correct these and other weld defects using conventional processes can be time consuming and expensive. Some of the weld defects may be located within the thickness of the weld and not visible to the naked eye on the surface of the weld. The use of TCT imaging using the secondary x-rays described herein allows generation of three-dimensional cross-sectional images which can include through the thickness of the weld zone and areas surrounding the weld zone allowing all defects, including those located within the thickness of the weld, to be detected.

The overall process of electron beam welding is well known to those of ordinary skill in the art. Parts to be welded and forming the workpiece are precisely aligned and placed inside a vacuum chamber. An electron beam of a desired current A, for example about 1 to about 1000 milliamps, accelerated by a desired voltage V, for example about 10 to about 500 kV, is focused into the junction of the parts, depositing high power P=AV in a very small volume, for example about $10^5$ to about $10^7$ W/mm$^3$. This raises the temperature in the working volume to, for example, about $10^8$ to about $10^{10}$ K/s. The workpiece is moved and/or the electron beam is scanned along the junction to create the weld. Depending on the beam parameters and speed of movement, this can produce a shallow weld, a deep, a wide weld or a narrow weld.

Figure 3:
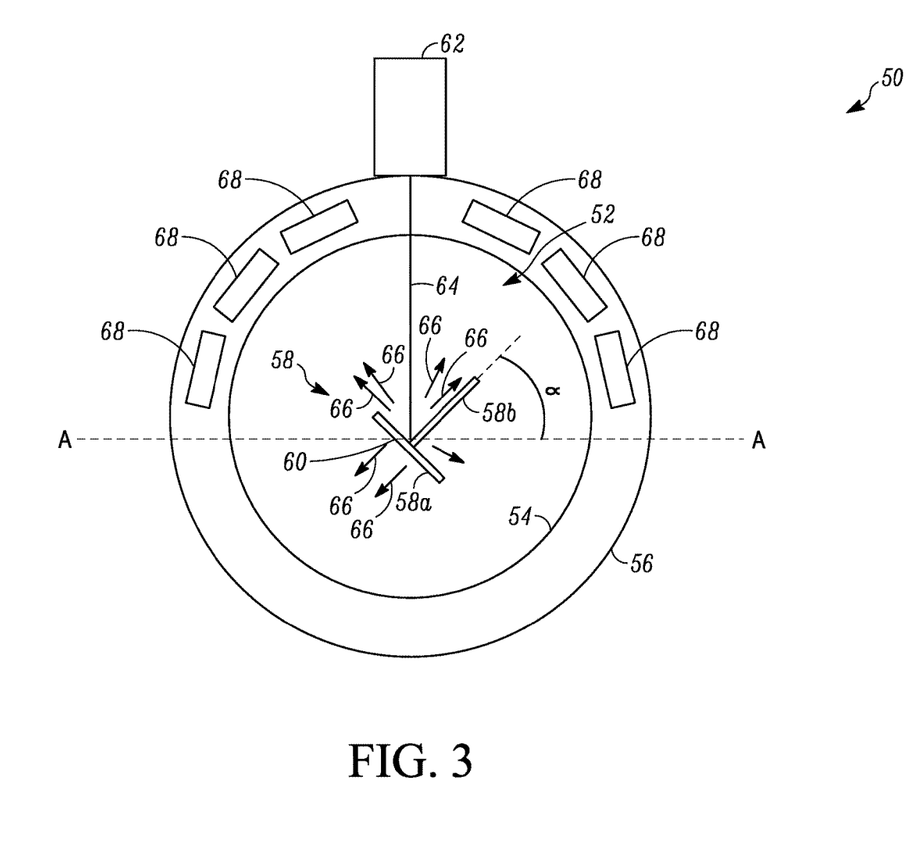
FIG. 3 is a schematic illustration of an electron beam welding apparatus that can utilize the processes described herein.

With reference to FIG. 3, an electron beam welding apparatus 50 that can perform electron beam welding employing the process 10 described above is illustrated. The apparatus 50 includes a vacuum chamber 52 defined by an inner wall 54 and an outer wall 56. The vacuum chamber 52 is illustrated as being circular from the view shown in FIG. 3 which is an end view of the vacuum chamber. In three-dimensions, the vacuum chamber can be cylindrical or spherical in shape. However, other shapes of the vacuum chamber 52 are possible, including rectangular as discussed below with respect to FIG. 4. Inside the vacuum chamber 52, a workpiece 58 is mounted on a fixture (not shown) of known construction. The workpiece 58 is formed by two structures 58a, 58b that are to be welded to one another along at least one joint 60. An electron beam generator 62 is mounted on the vacuum chamber 52 for producing an electron beam 64 and directing the electron beam 64 onto the joint 60.

In one embodiment, the fixture on which the workpiece 58 is mounted can move relative to the electron beam 64 to scan the beam 64 along the desired length of the joint 60 to be welded. In another embodiment, the fixture is stationary, and a beam controller is provided to scan the beam 64 along the desired length of the joint 60 to be welded. In still another embodiment, both the fixture can move and a beam controller is provided to cause the beam to be moved along the desired length of the joint 60 to be welded.

The weld at the joint 60 can be created from the materials of the two structures 58a, 58b without introduction of an additive material. In another embodiment, an additive weld material can be introduced into the process which is contacted and melted by the beam 64 and deposited at the joint 60 to form the weld. The additive weld material can initially be in solid form or in powder form prior to being melted or liquified by the electron beam 64.

When the beam 64 contacts the workpiece 58, secondary x-rays 66 are generated as shown by the arrows in FIG. 3. The secondary x-rays 66 travel through the workpiece surrounding the impact point, the fixture supporting the workpiece 58, and other elements in the apparatus 50, as discussed above.

One or more sensor arrays 68 can be provided on the apparatus 50 in order to detect the secondary x-rays 66. The number of sensor arrays 68 used, the shape of the arrays 68 and their locations, can vary. However, there should be a sufficient number of sensor arrays 68 that are located to permit subsequent generation of the three-dimensional cross-sectional images from the detected secondary x-rays 66. As shown in FIG. 3, relative to a horizontal axis A-A, in one embodiment there can be sensor arrays 68 that are arranged at angles α that range from about 30 degrees to about 60 degrees on one or both sides relative to the beam 64. In another embodiment, the sensor arrays 68 can be arranged at about 45 degrees relative to the axis A-A. However, the arrays 68 can be arranged at any angle(s) sufficient to permit subsequent generation of the three-dimensional cross-sectional image.

In the example illustrated in FIG. 3, the sensor arrays 68 are arranged between the inner wall 54 and the outer wall 56 of the apparatus 50. The inner wall 54 is x-ray transparent, or x-ray transparent solely at the locations of the sensor arrays 68, to permit transmission of the secondary x-rays through the inner wall 54 to the sensor arrays 68. The sensor arrays 68 can be mounted to the inner wall 54, or mounted to the outer wall 56. The sensor arrays 68 can also be mounted in a manner to permit the locations of the sensor arrays 68 to be changed which can be useful depending upon the shape of the workpiece 58, the shape of the fixture supporting the workpiece 58, strength of the electron beam 64, and other factors.

In operation, the electron beam 64 is directed onto the workpiece 58 to create a weld along the joint 60. The electron beam 64 has sufficient energy so that the secondary x-rays 66 are generated when the electron beam 64 contacts the workpiece 58. The secondary x-rays 66 are detected by the x-ray sensor arrays 68 in real-time as the welding proceeds. TCT is then used to generate the real-time three-dimensional cross-sectional images of the weld zone and surrounding area of the workpiece 58 as the welding progresses. The generated real-time three-dimensional cross-sectional images allow real-time detection of weld defects throughout the entire, substantially the entire, or a portion of the weld zone including defects located within the thickness of the weld that are not located on or visible at the surface of the weld. Real-time image processing (automated and/or man-in-the-loop) is then performed to detect welding flaws. In the case of automated analysis, if a defect is detected, control logic can be used to determine an optimal re-work strategy of the part of the weld containing the defect. In the case of human analysis, an operator can intercede in the processing and dictate re-work of the part of the weld containing the defect. If a defect is detected, an electron beam, such as the electron beam 64, can be automatically steered and/or the workpiece can be mechanically moved to re-work the weld.

In another embodiment, one or more separate electron beams different from the electron beam 64 can be used to conduct the re-work. Therefore, as the electron beam 64 continues along the joint 60 creating the weld, one or more separate electron beams, which can be generated by the electron beam generator 62 or by one or more separate electron beam generators, can be used to simultaneously re-work any areas of the weld containing a defect.

Figure 5:
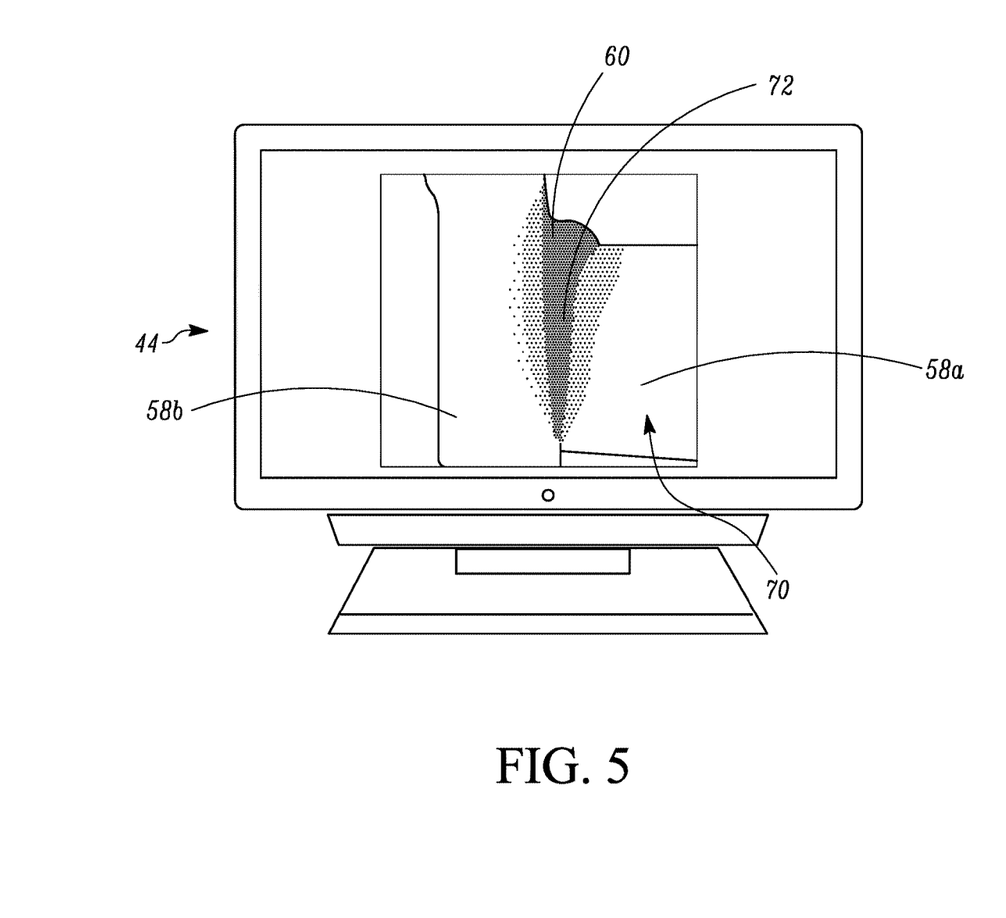

FIG. 5 illustrates the display device 44 that is displaying an example representation of what a three-dimensional cross-sectional image 70 that is generated as described herein may look like if the three-dimensional cross-sectional image is optionally displayed. In this example, the three-dimensional cross-sectional image 70 includes portions of the two structures 58a, 58b that form the workpiece, along with a portion of the joint 60 between the structures 58*a*, 58*b*. A portion of a weld zone 72 that is created by the electron beam is also depicted. The image 70 depicts the depth of the weld zone 72 into the structure 58*b* allowing defects within the depth of the weld zone 72 to be visualized. As with conventional TCT imaging processes, for example as used in the medical field, the image 70 that is displayed can be changed automatically or by a human operator, or the image 70 can be automatically or maneuvered by a human operator on the display device 44, to permit viewing of different portions of the weld zone and surrounding areas or viewing from different angles.

Therefore, the welding, image generation and analysis, and re-working can occur in real-time without having to allow the workpiece to cool before inspection and without having to remove the workpiece from the apparatus 50. An added benefit is that the generated TCT images of the finished weld can provide an inspection record detailing the quality of the weld.

Example Application—Electron Beam Additive Manufacturing

The use of an electron beam in additive manufacturing is described in U.S. Pat. No. 8,809,780 and U.S. Pat. No. 6,401,001, each of which is incorporated herein by reference in its entirety. The process 10 described above can be used in electron beam additive manufacturing by detecting the secondary x-rays during additive manufacturing for real-time TCT imaging, combined with real-time analysis and re-working to detect and correct defects in real-time.

Defects in creating a layer in additive manufacturing can result in a poor quality resulting manufactured product. Examples of layer defects that can arise in electron beam additive manufacturing can include, but are not limited to, void or cavities, gas porosity, excess penetration by the electron beam, and defects caused by electron gun discharge. Some of the defects may be located within the thickness of the added layer and may not be visible to the naked eye on the surface of the layer. The use of TCT imaging using the secondary x-rays described herein allows generation of three-dimensional cross-sectional images which includes through the thickness of the layer allowing all defects, including those located within the thickness of the layer, to be detected.

The overall process of electron beam additive manufacturing is well known to those of ordinary skill in the art and as described in U.S. Pat. No. 8,809,780 and U.S. Pat. No. 6,401,001. Raw material to be used to form the manufactured part is located inside a vacuum chamber. An electron beam is directed onto the raw material which partially melts or liquifies the raw material which is deposited in a layer into the shape of the desired part. This process is repeated, layer-by-layer, to complete the shape of the desired part. Examples of commercial additive manufacturing apparatus that can be used with the process described above include, but are not limited to, the Arcam A2 available from Arcam AB of Mölndal, Sweden, and the Sciaky VX-110 Electron Beam Advanced Manufacturing (EBAM) System available from Sciaky Inc. of Chicago, Ill.

Figure 4:
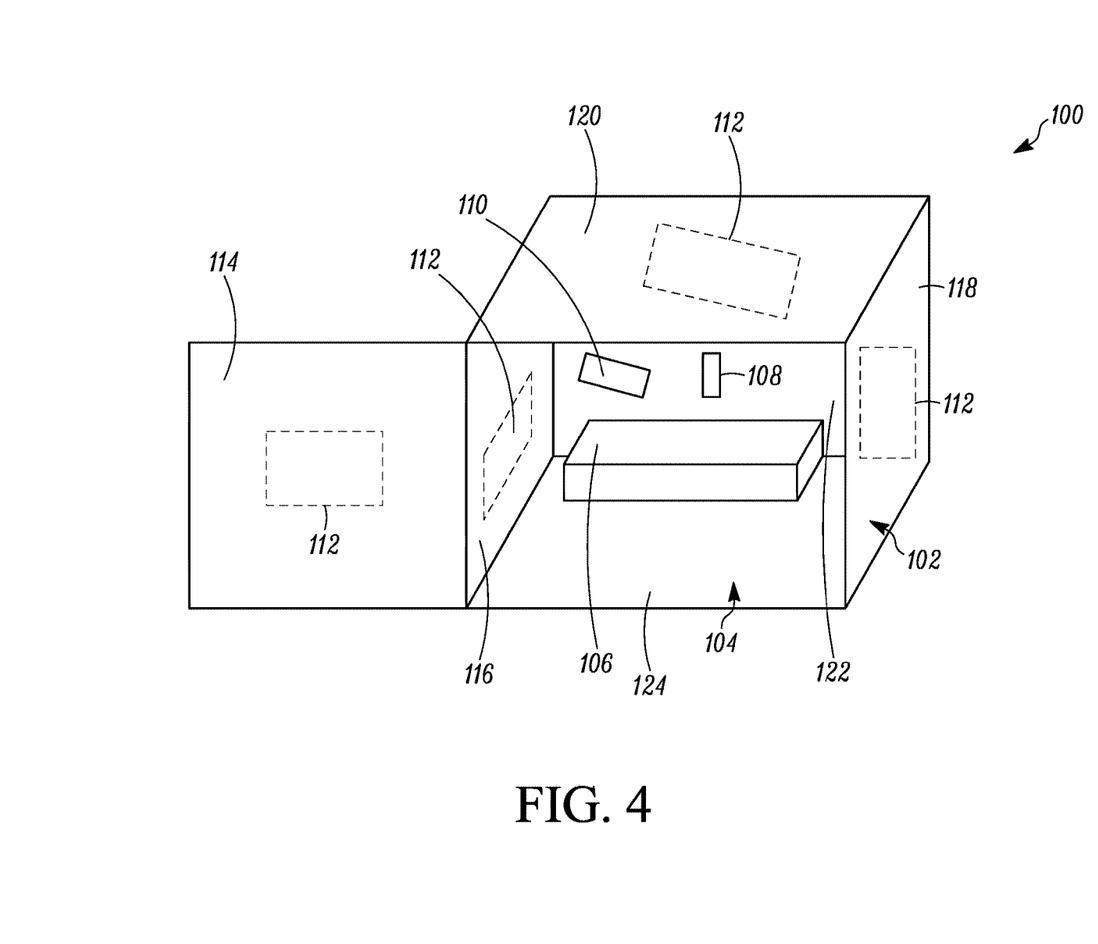
FIG. 4 is a schematic illustration of an electron beam additive manufacturing apparatus that can utilize the processes described herein.

With reference to FIG. 4, an apparatus 100 that can perform electron beam additive manufacturing employing the process 10 described above is illustrated. The apparatus 100 is similar in construction to the apparatus described in U.S. Pat. No. 8,809,780, and includes a generally rectangular housing 102 defining a vacuum chamber 104. Inside the vacuum chamber 104, a workpiece support (not shown) is provided on which a workpiece 106 is mounted. The workpiece 106 ultimately forms the intended manufactured part by adding multiple layers to the workpiece. The layer that is being created at any moment in time can be considered the workpiece described herein. An electron beam generator 108 is mounted within the vacuum chamber 104 for producing the electron beam. In addition, an additive feed mechanism 110 can be provided for feeding raw additive material to be used for creating each layer. The additive material provided by additive feed mechanism 110 can initially be in solid form or in powder form prior to being partially melted or liquified by the electron beam.

In one embodiment, the workpiece support on which the workpiece 106 is mounted can move relative to the electron beam to allow deposit of the material at appropriate locations on the workpiece. In another embodiment, the workpiece support is stationary, and a beam controller is provided to scan the electron beam generator 108 and the electron beam emitted therefrom over the workpiece. In addition, the additive feed mechanism 110 can move with the electron beam generator. In still another embodiment, the workpiece support, the electron beam generator 108 and the additive feed mechanism 110 can move.

When the electron beam is directed toward the workpiece, it partially melts or liquifies the additive material which is then deposited onto the workpiece. The electron beam also contacts the deposited material generating secondary x-rays which scatter as described above.

Returning to FIG. 4, one or more sensor arrays 112 can be provided on the apparatus 100 in order to detect the secondary x-rays. The number of sensor arrays 112 used, the shape of the arrays 112 and their locations, can vary. However, there should be a sufficient number of sensor arrays 112 that are located to permit subsequent generation of the three-dimensional cross-sectional images from the detected secondary x-rays. As shown in FIG. 4, in one embodiment there can be a sensor array 112 mounted on an openable and closeable front wall 114, a first side wall 116, a second side wall 118, a top wall 120, a rear wall 122, and optionally a bottom wall 124.

As with FIG. 3, the sensor arrays 112 can be arranged between inner and outer walls that form the walls 114-124. The inner wall is x-ray transparent, or x-ray transparent solely at the locations of the sensor arrays 112, to permit transmission of the x-rays through the inner wall to the sensor arrays 112. The sensor arrays 112 can be mounted to the inner wall, or mounted to the outer wall. The sensor arrays 112 can also be mounted in a manner to permit the locations of the sensor arrays 112 to be changed which can be useful depending upon the shape of the workpiece 106, the shape of the workpiece support supporting the workpiece 106, strength of the electron beam, and other factors.

In operation, the electron beam is directed toward the workpiece which partially melts or liquifies the additive material that is then deposited onto the workpiece. The electron beam also contacts the deposited material. The electron beam has sufficient energy so that the secondary x-rays are generated when the electron beam contacts the deposited material. The secondary x-rays are detected by the x-ray sensor arrays 112 in real-time as the additive layering proceeds. TCT is then used to generate real-time three-dimensional cross-sectional images of the layer as the layering progresses. The entire width and thickness of the deposited layer can be included in the images, allowing real-time detection of defects throughout the entire layer including defects located within the thickness of the layer that are not located on or visible at the surface of the layer. Real-time image processing (automated and/or man-in-the-loop) is then performed to detect any defects in the layer. In the case of automated analysis, if a defect is detected, control logic can be used to determine an optimal re-work strategy of the part of the layer containing the defect. In the case of human analysis, an operator can intercede in the processing and dictate re-work of the part of the layer containing the defect. If a defect is detected, the electron beam can be automatically steered and/or the workpiece can be mechanically moved to re-work the layer. Re-working can include, but is not limited to, re-melting the bulk material. This allows cavities or voids to collapse, gas bubbles (porosity) to escape, etc. Depending on the location of the defect, the layer most recently deposited can be re-melted, or melting may occur deeper, for example if the defect is on the boundary of the new layer and the one below it.

In another embodiment, one or more separate electron beams different from the electron beam used to liquify the additive can be used to conduct the re-work. Therefore, as the first electron beam continues along creating the layer, one or more separate electron beams, which can be generated by the electron beam generator 108 or by one or more separate electron beam generators, can be used to simultaneously re-work any areas of the layer containing a defect.

Therefore, the layering, image generation and analysis, and re-working can occur in real-time. An added benefit is that the generated TCT images can provide an inspection record detailing the quality of the manufactured product.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A process of detecting and correcting a defect during an electron beam manufacturing process on a workpiece, comprising:
    as an electron beam is directed onto a portion of the workpiece with sufficient energy to generate secondary x-rays, detecting the secondary x-rays generated from the electron beam contacting the portion of the workpiece;
    in real-time, using transmission computed tomography to generate from the detected secondary x-rays a three-dimensional cross-sectional image of the workpiece adjacent the portion thereof contacted by the electron beam;
    in real-time, analyzing the generated three-dimensional cross-sectional image to detect a defect in the workpiece; and
    thereafter using a correction electron beam to re-work the workpiece containing the detected defect without conducting a separate inspection of the workpiece.

2. The process of claim 1, wherein the electron beam manufacturing process is electron beam welding where the electron beam is used to weld two structures to each other.

3. The process of claim 1, wherein the electron beam manufacturing process is an electron beam additive manufacturing process where a structure is constructed by adding material to the structure layer-by-layer.

4. The process of claim 1, comprising using the electron beam to structurally modify the portion of the workpiece.

5. The process of claim 1, wherein the analyzing is automated analysis and/or human analysis.

6. A system of detecting and correcting a defect during an electron beam manufacturing process on a workpiece, comprising:
    an electron beam generator that generates an electron beam;
    a vacuum chamber containing the workpiece;
    an array of x-ray sensors that sense secondary x-rays produced by an electron beam generated by the electron beam generator contacting the workpiece; and
    an image generator connected to the array of x-ray sensors that generates a three-dimensional cross-sectional image from detected secondary x-rays using transmission computed tomography.

7. The system of claim 6, wherein the electron beam generator is part of an electron beam welder.

8. The system of claim 6, further comprising a defect detector connected to the image generator that detects defects, and an electron beam controller connected to the defect detector and to the electron beam generator to control the electron beam generator to re-work a portion of the workpiece determined to have a defect.

9. The system of claim 6, wherein the electron beam generator is part of an electron beam additive manufacturing apparatus.

* * * * *